United States Patent
Rakshit

(10) Patent No.: US 11,938,015 B2
(45) Date of Patent: Mar. 26, 2024

(54) BIOPRINTED TISSUE WITH THERAPY CAPABILITY

(71) Applicant: International Business Machines Corporation, Armonk, NY (US)

(72) Inventor: Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 980 days.

(21) Appl. No.: 16/879,973

(22) Filed: May 21, 2020

(65) Prior Publication Data
US 2021/0361406 A1    Nov. 25, 2021

(51) Int. Cl.
| | |
|---|---|
| A61F 2/04 | (2013.01) |
| G01L 1/16 | (2006.01) |
| G01L 1/18 | (2006.01) |
| G01L 5/101 | (2020.01) |
| G01L 5/162 | (2020.01) |
| G01N 27/04 | (2006.01) |
| A61F 2/48 | (2006.01) |

(52) U.S. Cl.
CPC .......... *A61F 2/04* (2013.01); *G01L 1/16* (2013.01); *G01L 1/18* (2013.01); *G01L 5/101* (2013.01); *G01L 5/162* (2013.01); *G01N 27/04* (2013.01); *A61F 2002/045* (2013.01); *A61F 2/482* (2021.08); *A61F 2240/002* (2013.01); *A61F 2250/0002* (2013.01); *A61F 2250/0096* (2013.01)

(58) Field of Classification Search
CPC ...... A61F 2/04; A61F 2/482; A61F 2002/045; A61F 2240/002; A61F 2250/0096; G01L 1/16; G01L 1/18; G01L 5/101; G01L 5/162; A61B 5/4851; G01N 27/04
See application file for complete search history.

(56) References Cited

U.S. PATENT DOCUMENTS

| | | | |
|---|---|---|---|
| 10,219,748 B2 | 3/2019 | Terry et al. | |
| 2015/0037445 A1* | 2/2015 | Murphy | C12M 33/12 425/131.1 |
| 2017/0181837 A1* | 6/2017 | Imran | A61F 2/04 |

FOREIGN PATENT DOCUMENTS

| | | | | |
|---|---|---|---|---|
| WO | WO-2018139890 A1 * | 8/2018 | ............. | A61F 2/042 |
| WO | 2019034008 A1 | 2/2019 | | |

OTHER PUBLICATIONS

Unknown, "Normal Movements of the Digestive Tract", About Motility—International Foundation for Gastrointestinal Disorders, Last Updated: Feb. 24, 2016, 5 pages.

Wengerter et al., "Three-Dimensional Printing in the Intestine", Clinical gastroenterology and hepatology: the official clinical practice journal of the American Gastroenterological Association 14(8), Abstract Only, May 2016, 3 pages.

(Continued)

*Primary Examiner* — Benjamin R Schmitt
(74) *Attorney, Agent, or Firm* — James L. Olsen

(57) ABSTRACT

A set of sensor data collected from one or more sensors associated with a bioprinted tissue is received. The set of sensor data is analyzed to determine whether a condition for controlled movement of the bioprinted tissue is met. A control signal is issued to a set of expansive elements to perform the controlled movement in response to determining that the condition for controlled movement of the bioprinted tissue is met.

18 Claims, 8 Drawing Sheets

(56) References Cited

OTHER PUBLICATIONS

Madden et al., "Bioprinted 3D Primary Human Intestinal Tissues Model Aspects of Native Physiology and ADME/Tox Functions", iScience, vol. 2, Apr. 2018, 31 pages.
Chowdhury, H., "Liver success holds promise of 3D organ printing", Special Report Scientific Research, Mar. 4, 2018, 6 pages.
Little et al., "Printing the future: 3D bioprinters and their uses", Australian Academy of Science, printed Apr. 27, 2020, 12 pages.
Unknown, "3D Bioprinting of Living Tissues", printed Apr. 27, 2020, 7 pages.
Bioninja, "Small Intestine", printed Apr. 27, 2020, 3 pages.
Huang et al., "Gut bioengineering promotes gut repair and pharmaceutical research: a review", Journal of Tissue Engineering, vol. 10, pp. 1-11, 2019.
Schneeberger et al., "Converging biofabrication and organoid technologies: the next frontier in hepatic and intestinal tissue engineering?", Biofabrication 9, 2017, 10 pages.
Wengerter et al., "Three-Dimensional Printing in the Intestine", Clinical Gastroenterology and Hepatology, May 4, 2016, 12 pages.
Mell et al., "The NIST Definition of Cloud Computing", Recommendations of the National Institute of Standards and Technology, Sep. 2011, 7 pages.

\* cited by examiner

BIOPRINTED TISSUE WITH THERAPY CAPABILITY

BACKGROUND

The present disclosure relates generally to the field of bioprinting, and in particular, to the fabrication of bioprinted body substitutes that include structural and software elements that facilitate integration and physical therapy of the transplanted body tissues.

3D printing is a process in which an object is physically constructed, typically by successively adding material layer by layer, based on a 3D model (e.g., a computer-aided design (CAD) model). A 3D printing process typically includes modeling (e.g., generating the size/shape of the object in computer software), printing (e.g., additive manufacturing based on the model), and finishing (e.g., sanding and painting the printed object). As advancements in the field of 3D printing are made, more complex materials are able to be constructed, including microelectronics (e.g., multi-material printing), tissues (e.g., bioprinting), and foods, to name a few. Additive manufacturing technologies currently meet fabrication needs in applications including medical devices, optics, microfluidics, aerospace components, fixturing, tooling, and others.

SUMMARY

Aspects of the present disclosure relate to a method, system, and computer program product for controlling a bioprinted tissue. A set of sensor data collected from one or more sensors associated with a bioprinted tissue can be received. The set of sensor data can be analyzed to determine whether a condition is met for a controlled movement of the bioprinted tissue. In response to determining that the condition for controlled movement of the bioprinted tissue is met, a control signal is issued to a set of expansive elements to perform the controlled movement.

The above summary is not intended to describe each illustrated embodiment or every implementation of the present disclosure.

BRIEF DESCRIPTION OF THE DRAWINGS

The drawings included in the present disclosure are incorporated into and form part of the specification. They illustrate embodiments of the present disclosure and, along with the description, serve to explain the principles of the disclosure. The drawings are only illustrative of typical embodiments and do not limit the disclosure.

Figure 1:
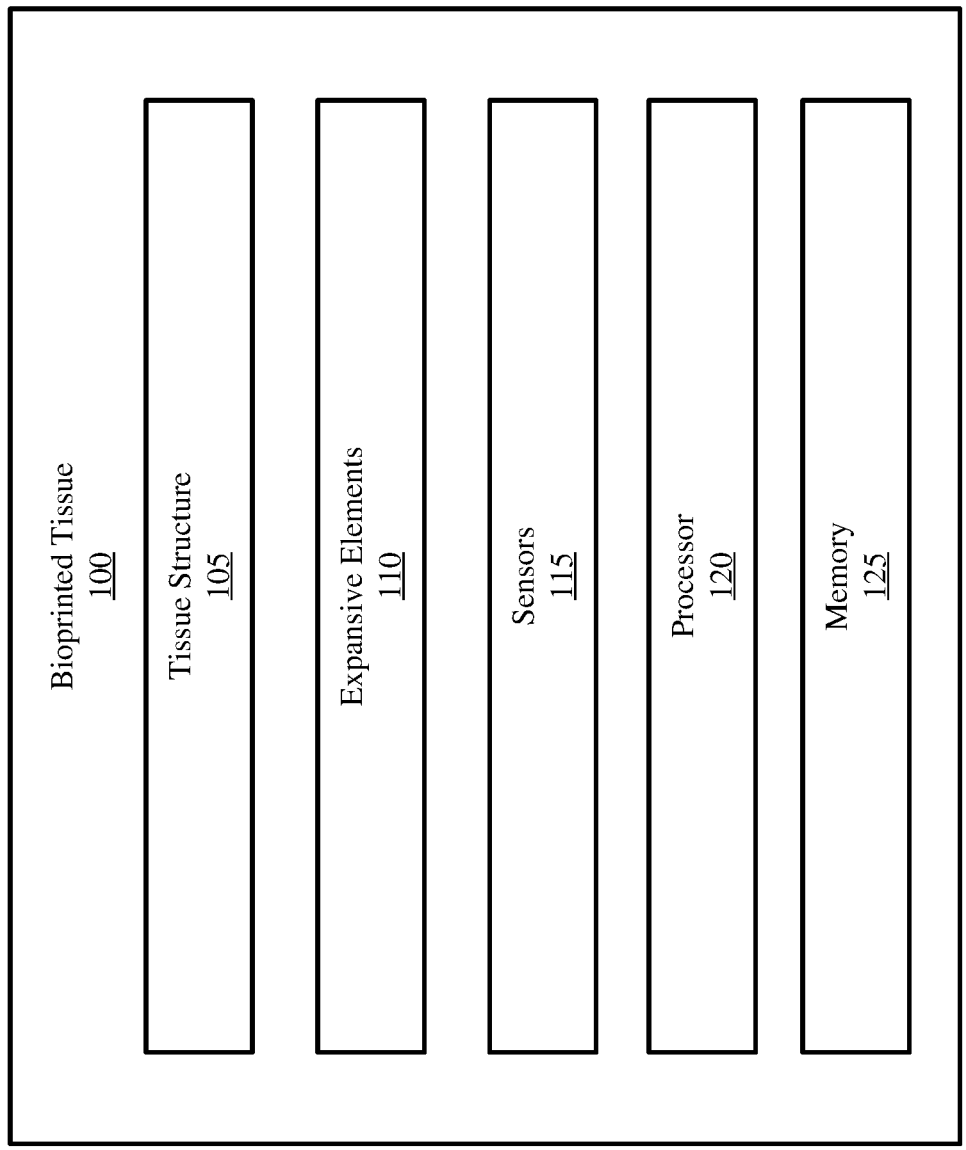
FIG. 1 is a block diagram illustrating components an example bioprinted tissue, in accordance with embodiments of the present disclosure

While the embodiments described herein are amenable to various modifications and alternative forms, specifics thereof have been shown by way of example, in the drawings and will be described in detail. It should be understood, however, that the particular embodiments described are not to be taken in a limiting sense. On the contrary, the intention is to cover all modifications, equivalents, and alternatives falling within the spirit and scope of the disclosure.

DETAILED DESCRIPTION

Aspects of the present disclosure relate generally to the field of bioprinting, and in particular, to the fabrication of bioprinted body substitutes that include structural and software elements that facilitate integration and physical therapy of the transplanted body tissues.

While the present disclosure is not necessarily limited to such applications, various aspects of the disclosure may be appreciated through a discussion of various examples using this context.

Bioprinting is a process that takes cells from donor organs and turns these cells into a printable bio-ink. Layers of cells are laid down in calculated designs to build up small sections of tissue. For example, bioprinting can be utilized to create artificial bone, skin, blood vessels, tongue tissue, and a variety of different internal organs. In one example method of bioprinting, the cells are taken from a person and cultured so that they can multiply. Then, the cultured cells are loaded into a specialized bioprinter. The cells are then layered, for example, using a hydrogel as a supporting structure. Finally, as layers of cells are printed into a three-dimensional (3D) structure, they grow into mature tissue and are able to be used for medical purposes. It should be appreciated that this is merely one example method of utilizing bioprinting to form tissues, and any suitable bioprinting method may be used in the context of the presently disclosed embodiments. That is, the bioprinting approach can be modified in any suitable manner to create various 3D tissues for regenerative medicine, drug testing endeavors, as well as body part transplantation.

The digestive tract includes the esophagus, the stomach, the small intestine, and the large intestine, among other components. Digestion involves the breakdown of food such that the food can be absorbed and assimilated into the body. The digestion process begins with chewing in the mouth. The food is then mixed with gastric acid and enzymes to facilitate further breakdown. Food moves through the digestive tract through a phenomenon known as peristalsis. Peristalsis is a rhythmic contraction and relaxation of muscles beginning at the esophagus and continuing through the rest of the gastrointestinal tract that results in the propagation of waves that facilitate the movement of food. As food traverses the digestive tract, nutrients are absorbed into the body.

Complications can occur when one or more portions of the digestive tract do not function as intended. For example, intestinal failure can result from the small intestine being too short (i.e., short bowel syndrome) or from functional failure (e.g., caused by disease or trauma). Though transplantation may be possible, the availability and compatibility of transplants are not guaranteed. Serious complications can occur if one or more components of the digestive tract are not functioning as intended. For example, life-threatening malnutrition can result from one or more tissues within the digestive tract not functioning as intended. Thus, fabricating artificial tissue which can perform one or more functions of digestive organs within the digestive tract can be greatly beneficial.

Aspects of the present disclosure relate to an artificial bioprinted tissue. A set of sensor data collected from one or more sensors associated with the bioprinted tissue can be received. The set of sensor data can be analyzed to determine whether a condition is met for a controlled movement of the bioprinted tissue. In response to determining that the condition for controlled movement of the bioprinted tissue is met, a control signal is issued to a set of expansive elements to perform the controlled movement. Controlled movements can include movements naturally performed by digestive tissues, including, without limitation, peristalsis, mixing, grinding, and churning.

Referring now to FIG. 1, shown is a high-level block diagram depicting elements of a bioprinted tissue 100, in accordance with embodiments of the present disclosure. The bioprinted tissue 100 includes a tissue structure 105, expansive elements 110, sensors 115, a processor 120, and a memory 125.

The tissue structure 105 of the bioprinted tissue 100 includes specialized cells (e.g., epithelial cells) organized into a tissue. The tissue structure 105 serves as the structure for which hardware components within the bioprinted tissue 100 are housed. For example, the expansive elements 110, sensors 115, processor 120, and memory 125 can be embedded in, attached to, housed within, or otherwise associated with the tissue structure 105 (e.g., before, during, or after a bioprinting process). In embodiments, the tissue structure 105 can be configured to at least partially perform one or more native functions of digestive tract tissue. For example, the tissue structure 105 can be configured to produce one or more proteins that facilitate nutrient absorption, signaling, and digestion.

The tissue structure 105 can be generated using a bioprinting process. For example, cells from a digestive tract organ or tissue (e.g., a donor source) can be used as printable bio-ink. The cells can then be dispensed layer-by-layer onto a biocompatible scaffold to generate a three-dimensional, tissue-like structure. However, the tissue structure 105 can be generated in any other suitable manner. For example, principles of biomimicry (e.g., duplication of the shape, framework, and microenvironment of the digestive tissue) or self-assembly (e.g., using stem-cells to automatically assemble into a tissue, which may be "scaffold-free") can be used to facilitate the generation of the tissue structure.

The expansive elements 110 can be used to control movements of the bioprinted tissue 100. In particular, data obtained from sensors 115 can be analyzed by the processor 120, such that the processor 120 can issue control signals to the expansive elements 110. The expansive elements 110 can then contract/expand based on the control signals issued by the processor 120 such that movement of the bioprinted tissue 100 can be controlled. In embodiments, the conditions for issuing control signals corresponding to different types of movements based on analyzed sensor data can be stored in memory 125. As such, if sensor data obtained from sensors 115 satisfies a condition stored in memory 125, the processor 120 can issue a corresponding control signal to the expansive elements 110. Thus, in embodiments, the expansive elements 110 can be embedded between cells of the tissue structure 105 (e.g., an inner and outer lining) such that the expansion and contraction of the tissue structure 105 can be controlled.

The expansive elements 110 can be any suitable actuator configured to control the movements of the bioprinted tissue 100. In some embodiments, the expansive elements 110 are spring devices that can be controlled using a programmatic magnetic force. The force exerted on the spring devices can be calculated in accordance with Hooke's Law, F=kD, where k is the spring constant and D is the compression/expansion amount after the force is applied. The force applied to each spring can be calculated by the processor 120 such that desired movements of the bioprinted tissue 100 can be achieved. In embodiments, magnetic coils can be coupled to the end of each spring device. In response to receiving a control signal from the processor 120, the magnetic coil can be temporarily magnetized by a particular amount such that a force "F" is generated on the spring, leading to a compression or expansion amount "D" based on the magnetic force. However, any suitable actuator can be implemented, including piezoelectric, hydraulic, thermal, pneumatic, electric, and mechanical actuators. Ultimately, the expansive elements 110 respond to a programmatic force such that they are configured to expand or contract by a particular distance.

Figure 3:
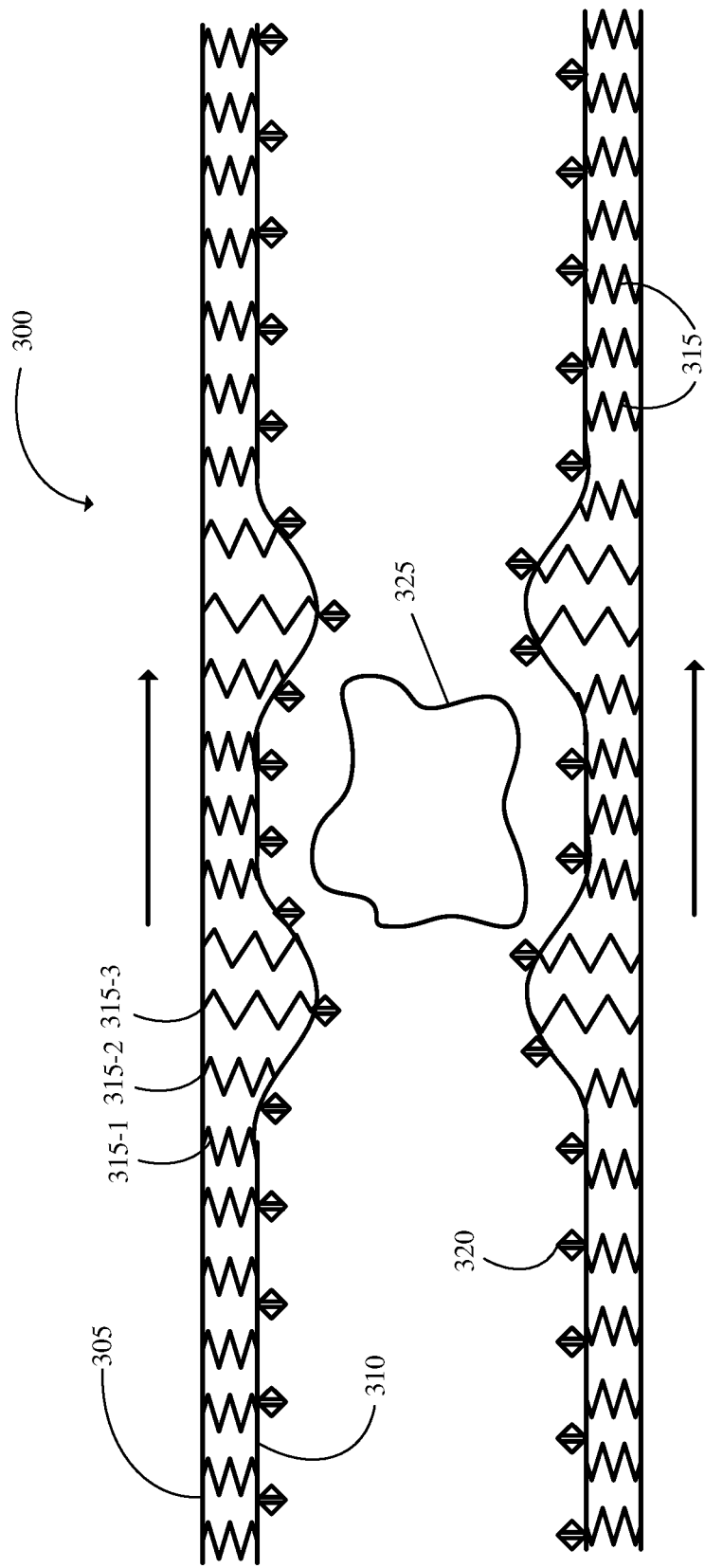
FIG. 3 is a diagram illustrating a cross-sectional view of a bioprinted tissue performing a peristalsis movement, in accordance with embodiments of the present disclosure.
Figure 4:
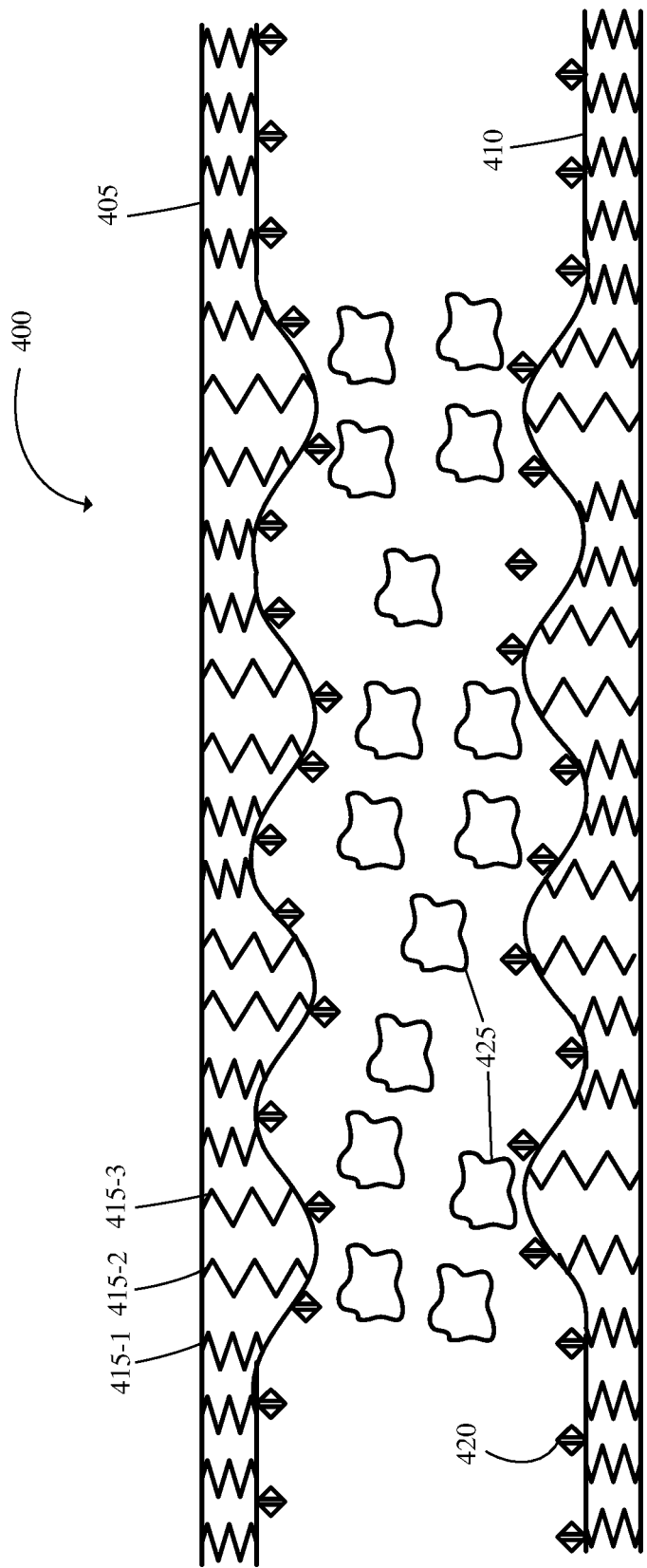
FIG. 4 is a diagram illustrating a cross-sectional view of a bioprinted tissue performing a mixing movement, in accordance with embodiments of the present disclosure.

In embodiments, the expansive elements 110 are organized into an array uniformly spread throughout the bioprinted tissue 100. For example, the expansive elements 110 can be uniformly spread (e.g., equal or similar spacing between each expansive element 110) along the circumference and length of the bioprinted tissue 100. This can allow orchestrated movements of the bioprinted tissue 100 by controlling a set of expansive elements 110 simultaneously. FIGS. 3-4 depict cross-sections of example movements that can be orchestrated by controlling the expansive elements.

Any suitable movement of the expansive elements 110 can be orchestrated by the processor 120. In some embodiments, mixing movements can be made, such that particulates (e.g., food in the process of digestion) within the bioprinted tissue 100 are mixed. This can aid in subjecting the particulates within the bioprinted tissue 100 to enzymes and/or acid within the tract. In some embodiments, grinding movements can be made, aiding with the breakdown of particulates within the bioprinted tissue 100. In some embodiments, peristalsis movements can be made, aiding to move the particulates through the bioprinted tissue 100.

The type of movement issued by the processor 120 can depend on the received sensor data. For example, the orchestrated movement can depend on the location within the bioprinted tissue 100 where sensor data is collected, the amount of force exerted on walls of the bioprinted tissue 100, the volume of matter within the bioprinted tissue 100, the viscosity of liquid within the bioprinted tissue 100, the density of matter within the bioprinted tissue 100, the temperature of contents within the bioprinted tissue 100, the concentration of chemical species within the bioprinted tissue 100, etc. As such, the type of sensor data, value of sensor data, and location of sensor data obtained from sensors 115 can dictate the type of movement to be orchestrated by the processor 120.

Any suitable sensors 115 can be implemented. In some embodiments, piezoelectric sensors can be used to detect force (e.g., by converting strain into electrical energy) exerted along the bioprinted tissue 100. The amount and location of forces detected within the bioprinted tissue 100 can be used to issue controlled movements to the expansive elements 110. For example, if a force is detected at a particular location within the bioprinted tissue 100, a control signal can be issued to expansive elements 110 at the location to cause a controlled movement. As another example, if a force is detected upstream (in a direction towards the mouth) within the bioprinted tissue 100, a control signal can be issued to expansive elements 110 downstream the bioprinted tissue 100 to cause a corresponding controlled movement. However, any other suitable sensors can be implemented, including optical sensors, thermal sensors, chemical sensors, biochemical sensors (e.g., protein, DNA, and RNA based probes), flow sensors, micro liquid density sensors (LDS), and others.

The expansive elements 110, sensors 115, processor 120, and memory 125 (collectively referred to as "hardware elements") can be incorporated into the bioprinted digestive tissue 100 in any suitable manner. In some embodiments, one or more hardware elements can be integrated into a scaffold prior to the deposition of the cells. In some embodiments, one or more hardware elements can be printed in combination with the deposition of cells (e.g., in a multi-material bioprinter). In some embodiments, one or more hardware elements can be added to the tissue structure 105 after the tissue structure 105 is fully formed (e.g., the cells have matured into a functioning tissue). In embodiments, the hardware elements are communicatively coupled using a control circuit (e.g., one or more electrical wires configured to bridge the hardware elements in the system). Thus, control signals can be issued by the processor 120 to each hardware element within the bioprinted tissue 100. Similarly, data can be received by the processor 120 from each hardware element within the bioprinted tissue 100. In embodiments, the hardware elements can be configured to receive wireless power. Thus, in embodiments, the control circuit can be coupled to a wireless power receiver (not shown). This can allow the bioprinted tissue to retain power to perform the various functions described above in an in vivo or in vitro environment.

It is noted that FIG. 1 is intended to depict the major representative components of an example bioprinted tissue 100. In some embodiments, however, individual components can have greater or lesser complexity than as represented in FIG. 1, components other than or in addition to those shown in FIG. 1 can be present, and the number, type, and configuration of such components can vary.

While FIG. 1 illustrates a bioprinted tissue 100 with a single processor 120 and memory 125, suitable computing environments for implementing embodiments of this disclosure can include any number of processors or memories. The various models, modules, systems, and components illustrated in FIG. 1 can exist, if at all, across a plurality of components. For example, some embodiments can include one or more remotely located processors and/or memories configured to analyze data collected from sensors 115. The remote processor(s) and/or memory(s) can communicate with the sensors 115 using any suitable communications connection (e.g., using a WAN, a LAN, a wired connection, an intranet, or the Internet). Further, though not shown, one or more external devices can be configured to supply wireless power to a wireless power receiver of the bioprinted tissue 100.

Figure 2:
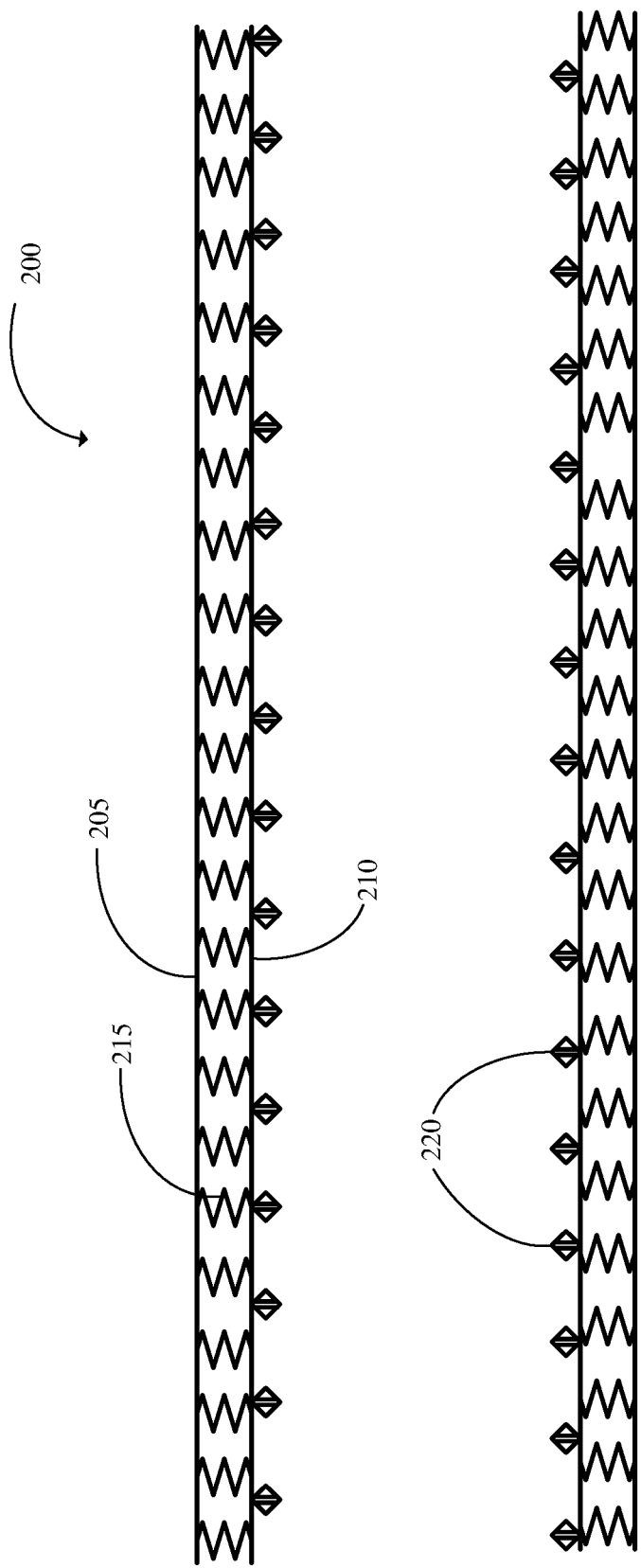
FIG. 2 is a diagram illustrating a cross-sectional view of a bioprinted tissue in a relaxed state, in accordance with embodiments of the present disclosure.

Referring now to FIG. 2, shown is a cross-sectional view of a bioprinted tissue 200 in a relaxed state, in accordance with embodiments of the present disclosure. The bioprinted tissue 200 can be the same as, or substantially similar to, the bioprinted tissue 100 of FIG. 1. Though not shown in FIG. 2, the bioprinted tissue 200 can include a processor and memory. Further, the bioprinted tissue 200 can have a cylindrical (e.g., tubular) shape, where food contents are housed within the cylinder, similar to the digestive tract of humans. Thus, FIG. 2 depicts a cross-section of a cylindrical-shaped bioprinted tissue 200, sliced along the length of the cylinder.

As depicted in FIG. 2, a plurality of expansive elements 215 are disposed between an outer layer 205 and an inner layer 210 of the bioprinted tissue 200. Thus, the expansion and/or contraction of the expansive elements 215 can cause the bioprinted tissue 200 to expand or contract in localized regions. However, as shown in FIG. 2, all expansive elements 215 are in a relaxed state. That is, no control signals have been transmitted by the processor to adjust the state of the expansive elements 215.

As depicted in FIG. 2, sensors 220 can be disposed along the inner layer 210 of the bioprinted tissue 200. The sensors 220 can be configured to collect sensor data such that the expansive elements 215 can be controlled. In embodiments, sensors 220 can be configured to collect data regarding the force exerted on the bioprinted tissue 200. This can be used to issue control signals to expansive elements 215, causing controlled movements at particular locations within the bioprinted tissue 200. However, sensors 220 can be located in any other suitable location, such as between the inner layer 210 and outer layer 205, along the outer layer 205, within the bioprinted tissue 200, etc. The location of sensors can depend on the type of sensors (e.g., thermal, viscosity, and liquid density sensors may be required to be disposed at least partially within the bioprinted tissue cavity, whereas force sensors may be required to be embedded on the interior layer of the bioprinted tissue).

The bioprinted tissue 200 can be configured to bend. This can be completed based on the elasticity of the bioprinted tissue-like structure. This can allow the bioprinted tissue 200 to bend and coil such that it can be compactly packaged. For example, the bioprinted tissue 200 can be any suitable length (e.g., 1 foot, 5 feet, 10 feet, 20 feet). The number of bends and/or coils can depend on the total length of the bioprinted tissue 200.

As discussed herein, a "control signal" issued by a processor configured to adjust the position of one or more expansive elements 215 within the bioprinted tissue 200 refers to a signal which activates the expansion or compression of the expansive elements 215. In embodiments where the expansive elements 215 are spring devices coupled to magnetic coils, the control signal can be the signal which causes the magnetic coils to magnetize and compress/expand the spring devices.

Referring now to FIG. 3, shown is a cross-sectional view of a bioprinted tissue 300 performing a peristalsis movement, in accordance with embodiments of the present disclosure. The bioprinted tissue 300 can be the same as, or substantially similar to, the bioprinted tissue 100 of FIG. 1 or the bioprinted tissue 200 of FIG. 2.

As depicted in FIG. 3, a peristalsis movement is being orchestrated by a processor of the bioprinted tissue 300. That is, expansive elements 315 in between an outer layer 305 and inner layer 310 of the bioprinted tissue 300 are expanding in a controlled manner such that a peristalsis motion causes a particulate 325 to move downstream the bioprinted tissue 300. The movement direction is depicted by arrows above and below the bioprinted tissue 300.

In embodiments, the peristalsis movement can be initiated in response to a sensor data condition. That is, sensor data collected by sensors 320 can be compared to conditions stored in memory such that expansive elements 315 can be controlled. Each expansive element 315 can be activated individually based on the sensor data collected by the sensors 320. For example, based on sensor data, a first expansive element 315-1 maintains a relaxed state, a second expansive element 315-2 is expanded by a first amount, and a third expansive element 315-3 is expanded by a second amount (greater than the first amount). Expansive elements 315 downstream are controlled in a similar manner such that a peristalsis movement is emulated within the bioprinted tissue 300, causing the particulate 325 to move downstream (towards the colon).

Referring now to FIG. 4, shown is a cross-sectional view of a bioprinted tissue 400 performing a mixing movement, in accordance with embodiments of the present disclosure. The bioprinted tissue 400 can be the same as, or substantially similar to, the bioprinted tissue 100 of FIG. 1, the bioprinted tissue 200 of FIG. 2, or the bioprinted tissue 300 of FIG. 3.

As depicted in FIG. 4, a mixing movement is being orchestrated by a processor of the bioprinted tissue 400. That is, expansive elements 415 in between an outer layer 405 and inner layer 410 of the bioprinted tissue 400 are expanding in a controlled manner such that a mixing motion causes a plurality of particulates 425 to be mixed within the bioprinted tissue 400. This can aid with exposing the particulates 425 to enzymes and/or chemicals within the bioprinted tissue 400 such that they can be digested. This can further aid with the breakdown of the particulates 425 based on the churning within the bioprinted tissue 400.

In embodiments, the mixing movement can be initiated in response to a sensor data condition. That is, sensor data collected by sensors 420 can be compared to conditions stored in memory such that expansive elements 415 can be controlled. Each expansive element 415 can be activated individually based on the sensor data collected by the sensors 420. For example, based on sensor data, a first expansive element 415-1 maintains a relaxed state, a second expansive element 415-2 is expanded by a first amount, and a third expansive element 415-3 is expanded by a second amount (less than the first amount). Expansive elements 415 upstream and downstream are controlled in a similar manner such that a mixing movement is emulated within the bioprinted tissue 400, causing the particulates 425 to churn within the bioprinted tissue 400.

Figure 5:
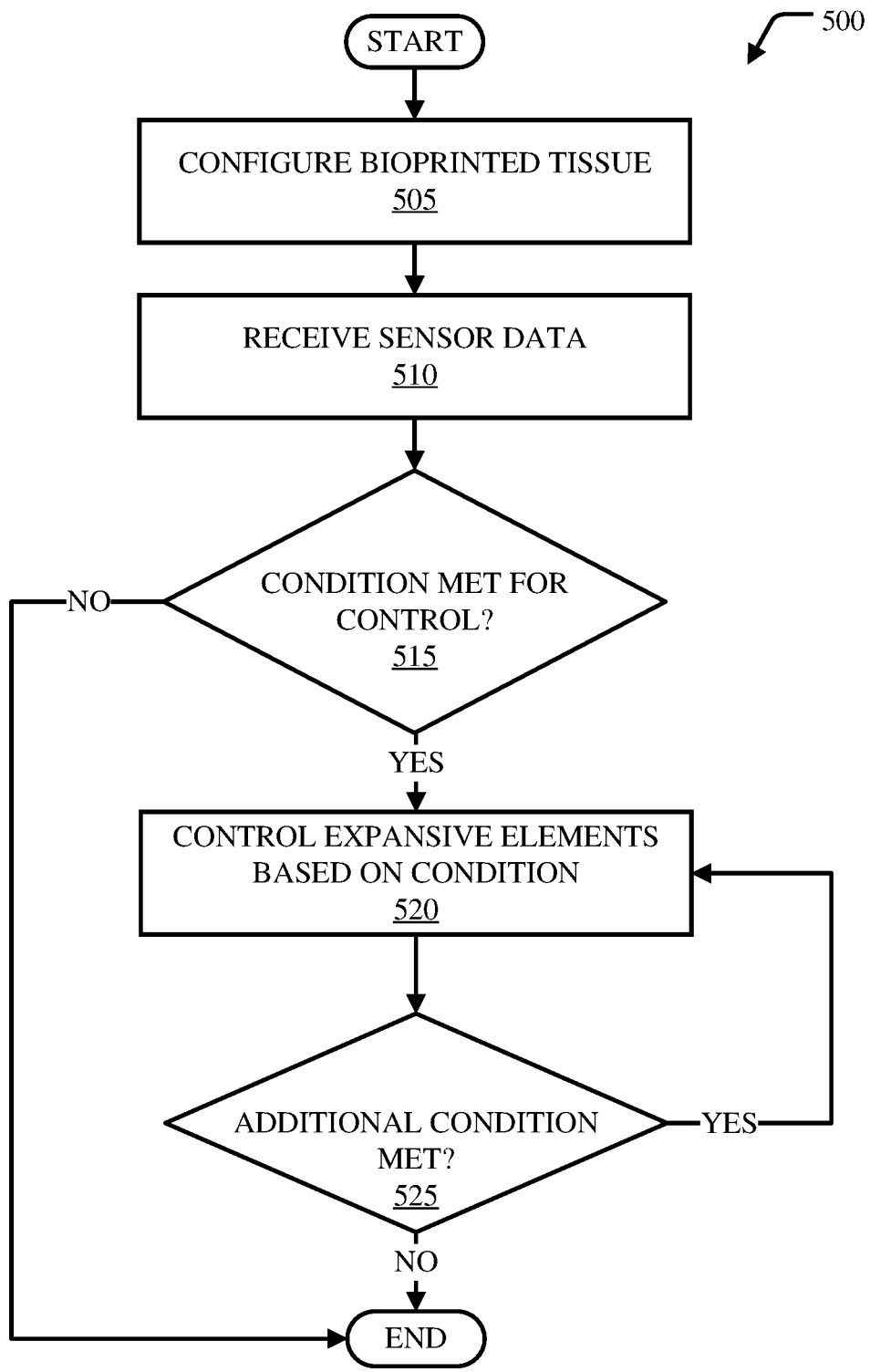
FIG. 5 is a flow diagram illustrating an example method for controlling a bioprinted tissue, in accordance with embodiments of the present disclosure.

Referring now to FIG. 5, shown is a flow diagram of an example method 500 for controlling a bioprinted tissue (e.g., bioprinted tissue 100, 200, 300, or 400), in accordance with embodiments of the present disclosure. The various operations of method 500 can be completed by one or more processing circuits (e.g., of a bioprinter and/or bioprinted tissue) and/or with the aid of manual intervention (e.g., a medical expert/scientist responsible for situating the bioprinted tissue in an in vivo or in vitro environment).

Method 500 initiates at operation 505, where a bioprinted tissue is configured. The bioprinted tissue can be formed using a bioprinting process, where cells are deposited into a scaffold and allowed to mature into a tissue (e.g., biomimicry) or alternatively where cells (e.g., stem cells) are exposed to stimuli such that they differentiate into a functioning tissue (e.g., self-assembly). Hardware elements (e.g., sensors, expansive elements, processors, memories, etc.) can be coupled to the tissue structure before (e.g., coupled to a scaffold prior to cell deposition), during (e.g., printed along with the cell deposition), or after (e.g., added to the matured tissue) the bioprinting process. Upon forming the bioprinted tissue with integrated hardware elements, the bioprinted tissue can be situated in vivo (e.g., within a living organism) or in vitro (e.g., in a lab setting, outside of a living organism).

Sensor data from one or more sensors of the bioprinted tissue is then received. This is illustrated at operation 510. Various sensors can be implemented into the bioprinted tissue. For example and without limitation, piezoelectric, chemical, biochemical, thermal, liquid density, liquid viscosity, and optical sensors can be implemented into the bioprinted tissue. Further, various conditions for controlling the bioprinted tissue can be stored in memory and referenced when analyzing sensor data. Thus, received sensor data can include any data collected from sensors used for the purpose of controlling the bioprinted tissue. Sensor data can include, without limitation, pressure data (e.g., forces exerted on the bioprinted tissue), temperature data, chemical data (e.g., collected from one or more chemical or biochemical probes), viscosity data, liquid density data, and optical data (e.g., visual data which can provide an indication regarding the volume of matter within the bioprinted tissue). Further, the time and location of the received sensor data can also be received and stored.

A determination is made whether a condition is met for control of the bioprinted tissue. This is illustrated at operation 515. As discussed above, various conditions corresponding to control mechanisms (e.g., movements) can be stored in memory. In response to one or more values collected from sensor data meeting a condition stored in memory, a corresponding control mechanism can be issued.

Any suitable control conditions can be implemented. In embodiments, one or more sensor value thresholds can be implemented such that if a particular sensor value exceeds or falls below a given threshold, a corresponding control mechanism can be issued to the expansive elements of the bioprinted tissue.

In embodiments, a force sensor value exceeding or falling below a threshold can lead to a control signal issued to one or more expansive elements to cause a controlled movement of the bioprinted tissue. For example, if a force sensor at a first location exceeds a force threshold, expansive elements upstream (e.g., by a particular distance), nearby (e.g., within a particular distance), or downstream (e.g., by a particular distance) the force sensor can be activated by the processor. In embodiments, the expansive elements can be controlled to produce a mixing, grinding, churning, or peristalsis movement.

In embodiments, ascertaining the presence of a particular chemical compound (and/or determining that the concentration of the chemical compound exceeds a threshold) within bioprinted tissue can be used to issue control signals to expansive elements by the processor. For example, if a first chemical, lactose, is identified using a biochemical probe coupled to the bioprinted tissue, then a mixing movement can be issued to expansive elements at the location where lactose was detected. This can aid in the breakdown of the lactose, by exposing the lactose to enzymes within the bioprinted tissue responsible for metabolizing the lactose. Control signals issued based on the presence and/or concentration of chemical species within the bioprinted tissue can be configured to produce any suitable movement (e.g., peristalsis, mixing, etc.) of the bioprinted tissue As another example, if the concentration of lactose exceeds a concentration threshold at a particular location within the bioprinted tissue, a control signal can be issued to expansive elements to produce a peristalsis movement such that the particulates containing lactose are moved downstream. This can be used to move the lactose-containing particulates towards enzymes responsible for metabolizing the lactose. Though reference is made to the chemical species lactose, aspects of the present disclosure recognize that the identification and/or concentration of any suitable chemical species can be used to control the expansive elements at particular locations within the bioprinted tissue.

In some embodiments, optical data (e.g., infrared data, X-ray data, camera data, etc.) can be used to issue control by the processor of the bioprinted tissue. For example, if an infrared radiation value exceeds or falls below a particular threshold, then a corresponding control value can be issued to expansive elements upstream (e.g., by a particular distance), nearby (e.g., within a particular distance), or downstream (e.g., by a particular distance) the infrared sensor to produce a controlled movement of the bioprinted tissue. Control signals can be issued based on any suitable optical data.

In embodiments, liquid density and/or viscosity data measured by a micro liquid density sensor (LDS) can be used to issue control by the processor of the bioprinted tissue. For example, in response to a liquid density or viscosity value exceeding or falling below a corresponding liquid density or viscosity threshold, a corresponding control signal can be issued to expansive elements upstream (e.g., by a particular distance), nearby (e.g., within a particular distance), or downstream (e.g., by a particular distance) to produce a controlled movement of the bioprinted tissue (e.g., peristalsis, mixing, etc.).

In embodiments, thermal data measured by a thermal sensor can be used to issue control signals by the processor of the bioprinted tissue. For example, if a thermal value collected by a thermal sensor falls below or exceeds a thermal threshold value, a corresponding control signal can be issued to expansive elements upstream (e.g., by a particular distance), nearby (e.g., within a particular distance), or downstream (e.g., by a particular distance) of the thermal sensor to produce a controlled movement of the bioprinted tissue.

In some embodiments, two or more sensor values collectively obtained from two or more corresponding sensors can be analyzed (e.g., averaged, added, etc.) and compared to one or more thresholds to control the bioprinted tissue. In some embodiments, a rate of change of sensor data can be compared to a rate of change threshold to control the bioprinted tissue.

With respect to control signals issued to control expansive elements of the bioprinted tissue, in embodiments, control signals issued by a processor coupled to the bioprinted tissue can be completed using proportional-integral-derivative (PID) control. That is, control can be based on proportional, integral, and/or derivative algorithms.

If a determination is made that a condition for controlling the bioprinted tissue is not met, then method 500 ends (as no conditions for controlling the bioprinted tissue are observed). If a determination is made that a condition for controlling the bioprinted tissue is met, then a corresponding control mechanism is issued by the processor to the expansive elements of the bioprinted tissue. This is illustrated at operation 520. The control mechanism can include the various movements described above (e.g., peristalsis of FIG. 3, mixing of FIG. 4, etc.) issued to particular locations within the bioprinted tissue. The locations which are controlled within the bioprinted tissue can depend on the location of sensor data, the value of sensor data, the type of sensor data, and other factors.

Upon controlling the expansive elements based on the condition, a determination is made whether any additional conditions are met. This is illustrated at operation 525. If additional conditions are met, then method 500 returns to operation 520, where control is issued to expansive elements based on the observed conditions. If no additional conditions are met, then method 500 ends, as no further control of the bioprinted tissue is necessary. In embodiments, method 500 may continually loop between operations 520 and 525 throughout the life of the bioprinted tissue.

The aforementioned operations can be completed in any order and are not limited to those described. Additionally, some, all, or none of the aforementioned operations can be completed while still remaining within the spirit and scope of the present disclosure.

It is to be understood that although this disclosure includes a detailed description on cloud computing, implementation of the teachings recited herein is not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure, including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure, including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
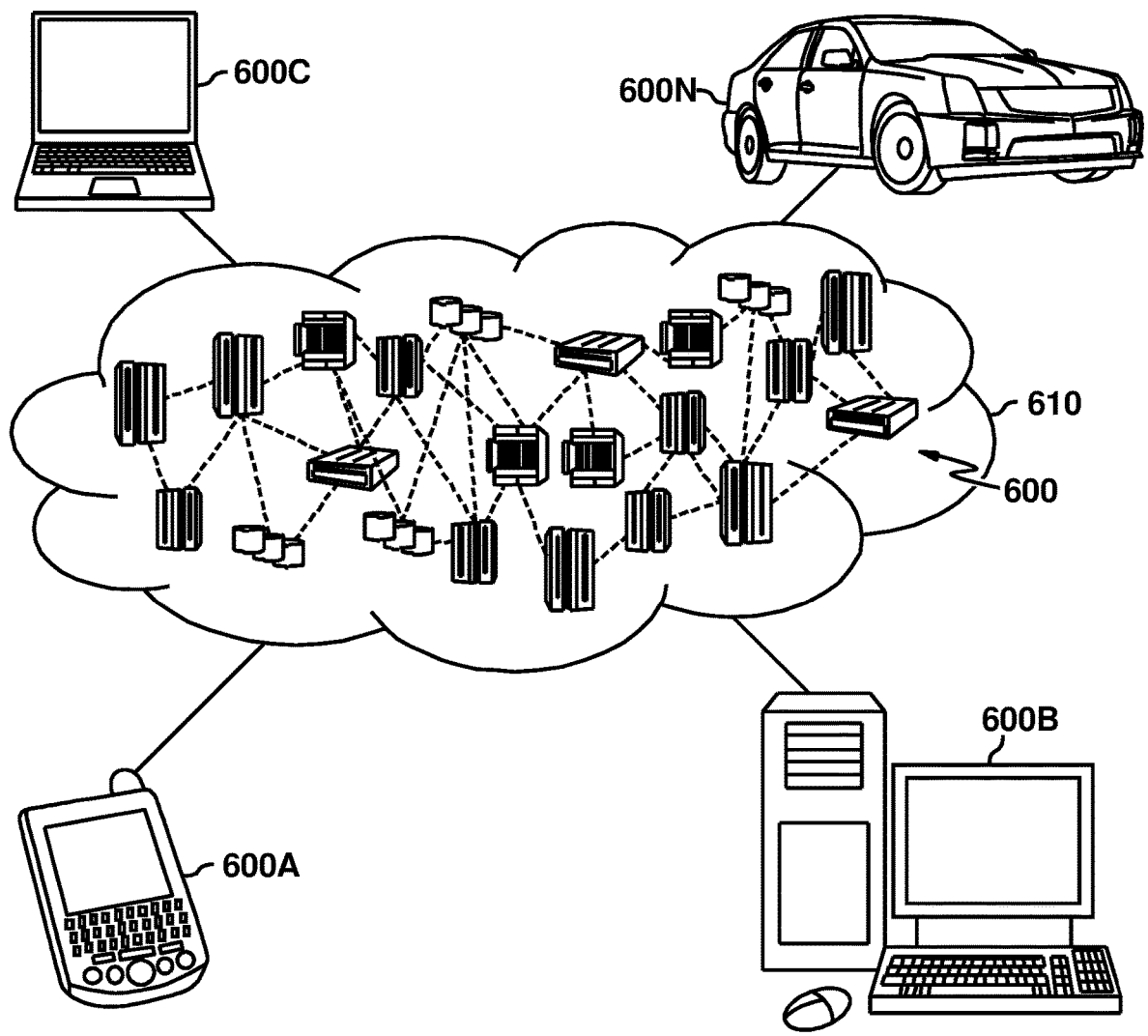
FIG. 6 is a diagram illustrating a cloud computing environment, in accordance with embodiments of the present disclosure.

Referring now to FIG. 6, illustrative cloud computing environment 610 is depicted. As shown, cloud computing environment 610 includes one or more cloud computing nodes 600 with which local computing devices used by cloud consumers, such as, for example, personal digital assistant (PDA) or cellular telephone 600A (e.g., a device configured to transmit wireless power to a wireless power receiver of bioprinted tissue 100), desktop computer 600B, laptop computer 600C (e.g., a device containing processor 120 or memory 125 configured to analyze sensor data received from bioprinted tissue 100), and/or automobile computer system 600N can communicate. Nodes 600 can communicate with one another. They can be grouped (not shown) physically or virtually, in one or more networks, such as Private, Community, Public, or Hybrid clouds as described hereinabove, or a combination thereof. This allows cloud computing environment 610 to offer infrastructure, platforms and/or software as services for which a cloud consumer does not need to maintain resources on a local computing device. It is understood that the types of computing devices 600A-N shown in FIG. 6 are intended to be illustrative only and that computing nodes 600 and cloud computing environment 610 can communicate with any type of computerized device over any type of network and/or network addressable connection (e.g., using a web browser).

Figure 7:
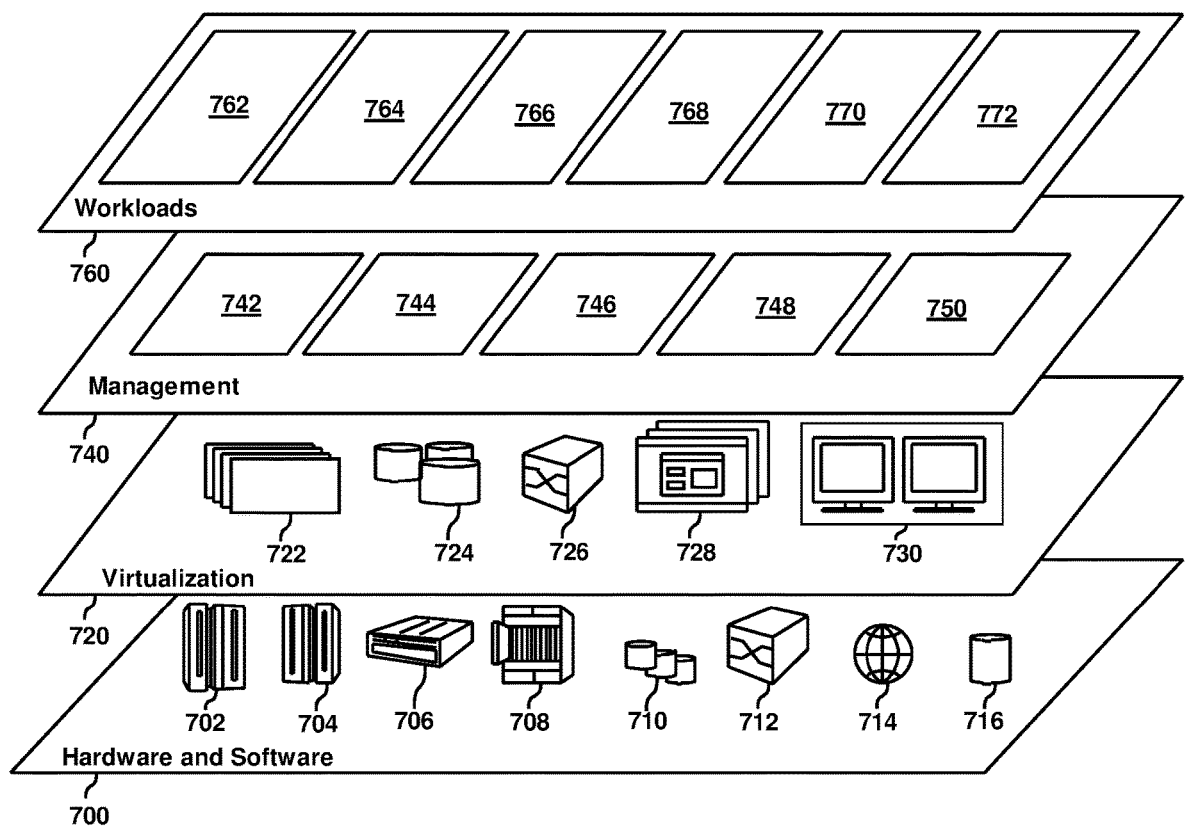
FIG. 7 is a block diagram illustrating abstraction model layers, in accordance with embodiments of the present disclosure.

Referring now to FIG. 7, a set of functional abstraction layers provided by cloud computing environment 610 (FIG. 6) is shown. It should be understood in advance that the components, layers, and functions shown in FIG. 7 are intended to be illustrative only and embodiments of the disclosure are not limited thereto. As depicted below, the following layers and corresponding functions are provided.

Hardware and software layer 700 includes hardware and software components. Examples of hardware components include: mainframes 702; RISC (Reduced Instruction Set Computer) architecture based servers 704; servers 706; blade servers 708; storage devices 710; and networks and networking components 712. In some embodiments, software components include network application server software 714 and database software 716.

Virtualization layer 720 provides an abstraction layer from which the following examples of virtual entities can be provided: virtual servers 722; virtual storage 724; virtual networks 726, including virtual private networks; virtual applications and operating systems 728; and virtual clients 730.

In one example, management layer 740 can provide the functions described below. Resource provisioning 742 provides dynamic procurement of computing resources and other resources that are utilized to perform tasks within the cloud computing environment. For example, resource provisioning 742 can allocate additional computing resources to devices which are indicated to have high activity. Metering and Pricing 744 provide cost tracking as resources are utilized within the cloud computing environment, and billing or invoicing for consumption of these resources. In one example, these resources can include application software licenses. In some embodiments, Metering and Pricing 744 indicates the number of allotted licenses to machines in the system. Security provides identity verification for cloud consumers and tasks, as well as protection for data and other resources. User portal 746 provides access to the cloud computing environment for consumers and system administrators. Service level management 748 provides cloud computing resource allocation and management such that required service levels are met. Service Level Agreement (SLA) planning and fulfillment 750 provide pre-arrangement for, and procurement of, cloud computing resources for which a future requirement is anticipated in accordance with an SLA.

Workloads layer 760 provides examples of functionality for which the cloud computing environment can be utilized. Examples of workloads and functions which can be provided from this layer include: mapping and navigation 762; image processing 764; natural language processing 766; classification 768; transaction processing 770; and sensor data processing 772.

Figure 8:
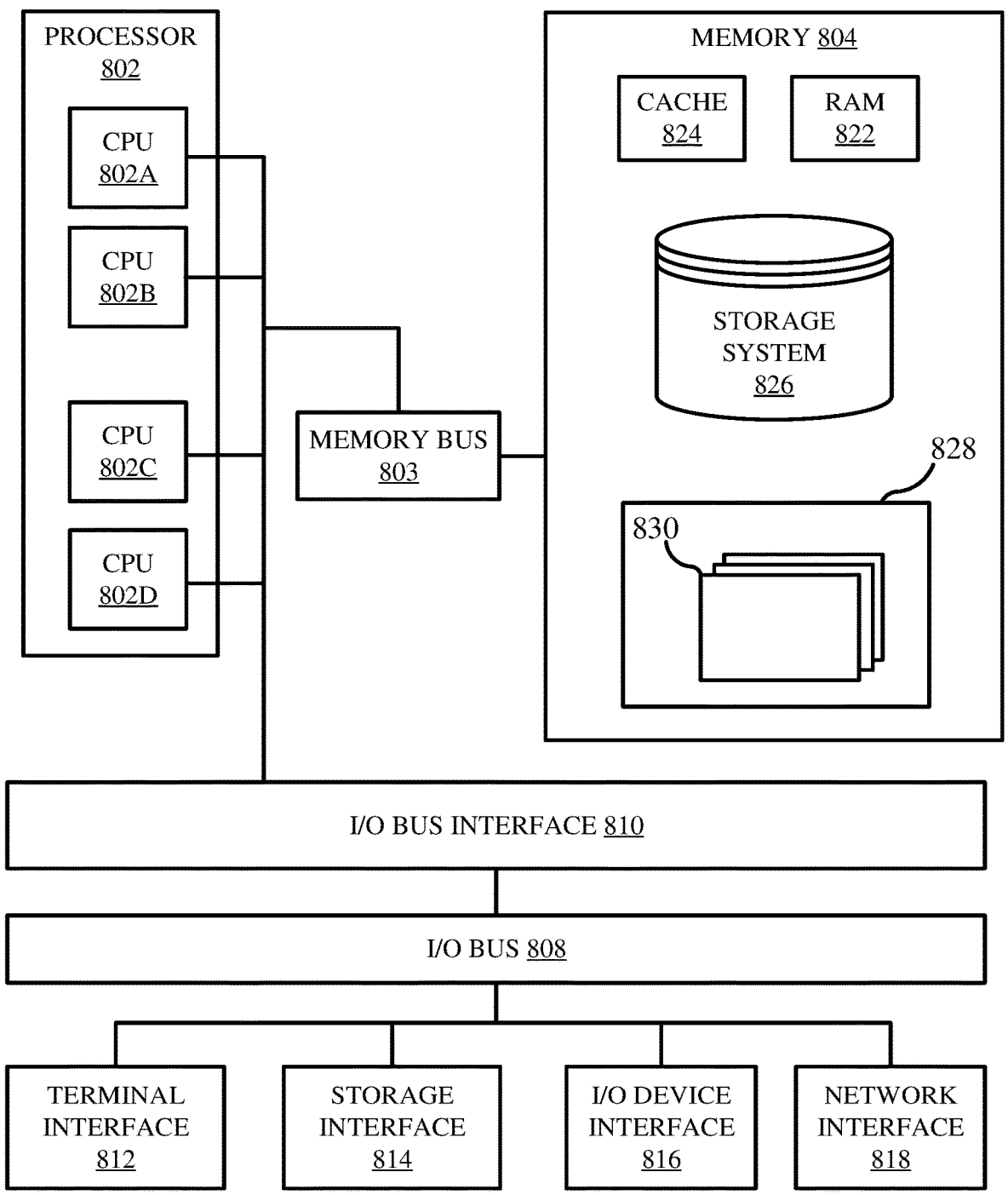
FIG. 8 is a high-level block diagram illustrating an example computer system that can be used in implementing one or more of the methods, tools, and modules, and any related functions described herein, in accordance with embodiments of the present disclosure.

Referring now to FIG. 8, shown is a high-level block diagram of an example computer system 801 that may be used in implementing one or more of the methods, tools, and modules, and any related functions, described herein (e.g., using one or more processor circuits or computer processors of the computer, such as processor 120 of FIG. 1), in accordance with embodiments of the present disclosure. In some embodiments, the major components of the computer system 801 may comprise one or more CPUs 802, a memory subsystem 804, a terminal interface 812, a storage interface

814, an I/O (Input/Output) device interface 816, and a network interface 818, all of which may be communicatively coupled, directly or indirectly, for inter-component communication via a memory bus 803, an I/O bus 808, and an I/O bus interface unit 810.

The computer system 801 may contain one or more general-purpose programmable central processing units (CPUs) 802A, 802B, 802C, and 802D, herein generically referred to as the CPU 802. In some embodiments, the computer system 801 may contain multiple processors typical of a relatively large system; however, in other embodiments the computer system 801 may alternatively be a single CPU system. Each CPU 802 may execute instructions stored in the memory subsystem 804 and may include one or more levels of on-board cache.

System memory 804 may include computer system readable media in the form of volatile memory, such as random access memory (RAM) 822 or cache memory 824. Computer system 801 may further include other removable/non-removable, volatile/non-volatile computer system storage media. By way of example only, storage system 826 can be provided for reading from and writing to a non-removable, non-volatile magnetic media, such as a "hard-drive." Although not shown, a magnetic disk drive for reading from and writing to a removable, non-volatile magnetic disk (e.g., a "USB thumb drive" or "floppy disk"), or an optical disk drive for reading from or writing to a removable, non-volatile optical disc such as a CD-ROM, DVD-ROM or other optical media can be provided. In addition, memory 804 can include flash memory, e.g., a flash memory stick drive or a flash drive. Memory devices can be connected to memory bus 803 by one or more data media interfaces. The memory 804 may include at least one program product having a set (e.g., at least one) of program modules that are configured to carry out the functions of various embodiments.

One or more programs/utilities 828, each having at least one set of program modules 830 may be stored in memory 804. The programs/utilities 828 may include a hypervisor (also referred to as a virtual machine monitor), one or more operating systems, one or more application programs, other program modules, and program data. Each of the operating systems, one or more application programs, other program modules, and program data or some combination thereof, may include an implementation of a networking environment. Programs/utilities 828 and/or program modules 830 generally perform the functions or methodologies of various embodiments.

Although the memory bus 803 is shown in FIG. 8 as a single bus structure providing a direct communication path among the CPUs 802, the memory subsystem 804, and the I/O bus interface 810, the memory bus 803 may, in some embodiments, include multiple different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface 810 and the I/O bus 808 are shown as single respective units, the computer system 801 may, in some embodiments, contain multiple I/O bus interface units 810, multiple I/O buses 808, or both. Further, while multiple I/O interface units are shown, which separate the I/O bus 808 from various communications paths running to the various I/O devices, in other embodiments some or all of the I/O devices may be connected directly to one or more system I/O buses.

In some embodiments, the computer system 801 may be a multi-user mainframe computer system, a single-user system, or a server computer or similar device that has little or no direct user interface, but receives requests from other computer systems (clients). Further, in some embodiments, the computer system 801 may be implemented as a desktop computer, portable computer, laptop or notebook computer, tablet computer, pocket computer, telephone, smart phone, network switches or routers, or any other appropriate type of electronic device.

It is noted that FIG. 8 is intended to depict the representative major components of an exemplary computer system 801. In some embodiments, however, individual components may have greater or lesser complexity than as represented in FIG. 8, components other than or in addition to those shown in FIG. 8 may be present, and the number, type, and configuration of such components may vary.

As discussed in more detail herein, it is contemplated that some or all of the operations of some of the embodiments of methods described herein may be performed in alternative orders or may not be performed at all; furthermore, multiple operations may occur at the same time or as an internal part of a larger process.

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the various embodiments. As used herein, the singular forms "a," "an," and "the" are intended to include the plural forms as well, unless the context clearly indicates otherwise. It will be further understood that the terms "includes" and/or "including," when used in this specification, specify the presence of the stated features, integers, steps, operations, elements, and/or components, but do not preclude the presence or addition of one or more other features, integers, steps, operations, elements, components, and/or groups thereof. In the previous detailed description of example embodiments of the various embodiments, reference was made to the accompanying drawings (where like numbers represent like elements), which form a part hereof, and in which is shown by way of illustration specific example embodiments in which the various embodiments may be practiced. These embodiments were described in sufficient detail to enable those skilled in the art to practice the embodiments, but other embodiments may be used and logical, mechanical, electrical, and other changes may be made without departing from the scope of the various embodiments. In the previous description, numerous specific details were set forth to provide a thorough understanding the various embodiments. But, the various embodiments may be practiced without these specific details. In other instances, well-known circuits, structures, and techniques have not been shown in detail in order not to obscure embodiments.

Different instances of the word "embodiment" as used within this specification do not necessarily refer to the same embodiment, but they may. Any data and data structures illustrated or described herein are examples only, and in other embodiments, different amounts of data, types of data, fields, numbers and types of fields, field names, numbers and types of rows, records, entries, or organizations of data may be used. In addition, any data may be combined with logic, so that a separate data structure may not be necessary. The previous detailed description is, therefore, not to be taken in a limiting sense.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Although the present disclosure has been described in terms of specific embodiments, it is anticipated that alterations and modification thereof will become apparent to those skilled in the art. Therefore, it is intended that the following claims be interpreted as covering all such alterations and modifications as fall within the true spirit and scope of the disclosure.

What is claimed is:

1. A method comprising:
receiving a set of sensor data collected from one or more sensors associated with a bioprinted tissue, wherein the set of sensor data includes chemical concentration data collected by at least one chemical sensor;
analyzing the set of sensor data to determine whether a condition for controlled movement of the bioprinted tissue is met; and
issuing, in response to determining that the condition for controlled movement of the bioprinted tissue is met, a control signal to a set of expansive elements to perform the controlled movement.

2. The method of claim 1, wherein the controlled movement is a peristalsis movement.

3. The method of claim 1, wherein the set of sensor data includes force data collected by at least one piezoelectric sensor.

4. The method of claim 3, wherein determining that the condition for controlled movement is met includes determining that a force sensor value exceeds a force threshold.

5. The method of claim 1, wherein determining that the condition for controlled movement is met includes determining that a concentration of a first chemical species exceeds a concentration threshold.

6. The method of claim 1, wherein issuing the control signal to the set of expansive elements includes issuing a first control signal to a first expansive element to expand by a first amount, issuing a second control signal to a second expansive element to expand by a second amount, and issuing a third control signal to a third expansive element to expand by a third amount.

7. A system comprising:
a bioprinted tissue, the bioprinted tissue including a plurality of sensors and a plurality of expansive elements;
one or more memories; and
one or more processors communicatively coupled to the one or more memories and the bioprinted tissue configured to perform a method, the method comprising:
receiving a set of sensor data from the one or more sensors of the bioprinted tissue, wherein the set of sensor data includes liquid density data collected by at least one liquid density sensor;
analyzing the set of sensor data to determine whether a condition for controlled movement of the bioprinted tissue is met; and
issuing, in response to determining that the condition for controlled movement of the bioprinted tissue is met, a control signal to a set of expansive elements to perform the controlled movement.

8. The system of claim 7, wherein the controlled movement is a mixing movement.

9. The system of claim 7, wherein determining that the condition for controlled movement is met includes determining that a liquid density value exceeds a liquid density threshold.

10. The system of claim 7, wherein the set of sensor data includes chemical concentration data collected by at least one chemical sensor.

11. The system of claim 10, wherein determining that the condition for controlled movement is met includes determining that a concentration of a first chemical species exceeds a concentration threshold.

12. The system of claim 7, wherein issuing the control signal to the set of expansive elements includes issuing a first control signal to a first expansive element to expand by a first amount, issuing a second control signal to a second expansive element to expand by a second amount, and issuing a third control signal to a third expansive element to expand by a third amount.

13. A computer program product comprising one or more computer readable storage media, and program instructions collectively stored on the one or more computer readable storage media, the program instructions comprising instructions configured to cause one or more processors to perform a method comprising:
receiving a set of sensor data collected from one or more sensors associated with a bioprinted tissue;
analyzing the set of sensor data to determine whether a condition for controlled movement of the bioprinted tissue is met; and
issuing, in response to determining that the condition for controlled movement of the bioprinted tissue is met, a control signal to a set of expansive elements to perform the controlled movement, wherein the set of expansive elements includes a magnetically actuated spring device.

14. The computer program product of claim 13, wherein the set of sensor data includes temperature data collected by at least one thermal sensor.

15. The computer program product of claim 14, wherein determining that the condition for controlled movement is met includes determining that a temperature value exceeds a temperature threshold.

16. The computer program product of claim 15, wherein determining that the condition for controlled movement is met includes ascertaining a presence of a first chemical species.

17. The computer program product of claim 13, wherein the set of sensor data includes chemical concentration data collected by at least one chemical sensor.

18. The computer program product of claim 13, wherein issuing the control signal to the set of expansive elements includes issuing a first control signal to a first expansive element to expand by a first amount, issuing a second control signal to a second expansive element to expand by a second amount, and issuing a third control signal to a third expansive element to expand by a third amount.

* * * * *